United States Patent
Kroll et al.

(10) Patent No.: US 8,812,103 B2
(45) Date of Patent: Aug. 19, 2014

(54) METHOD FOR DETECTING AND TREATING INSULATION LEAD-TO-HOUSING FAILURES

(71) Applicant: Lamda Nu, LLC, Orono, MN (US)

(72) Inventors: Mark William Kroll, Crystal Bay, MN (US); Charles Dennis Swerdlow, Brentwood, CA (US)

(73) Assignee: Lamda Nu, LLC, Orono, MN (US)

( * ) Notice: Subject to any disclaimer, the term of this patent is extended or adjusted under 35 U.S.C. 154(b) by 0 days.

(21) Appl. No.: 13/843,145

(22) Filed: Mar. 15, 2013

(65) Prior Publication Data

US 2013/0325080 A1 Dec. 5, 2013

Related U.S. Application Data

(60) Provisional application No. 61/689,191, filed on Jun. 1, 2012.

(51) Int. Cl.
*A61N 1/39* (2006.01)
*A61N 1/08* (2006.01)

(52) U.S. Cl.
CPC ......... *A61N 1/3931* (2013.01); *A61N 2001/083* (2013.01)
USPC .................................. 607/6; 607/63; 607/28

(58) Field of Classification Search
CPC ....................... A61N 2001/083; A61N 1/3931
See application file for complete search history.

(56) References Cited

U.S. PATENT DOCUMENTS

| | | |
|---|---|---|
| 3,599,055 A | 8/1971 | Bloom |
| 4,766,549 A | 8/1988 | Schweitzer, III et al. |
| 5,003,975 A | 4/1991 | Hafelfinger et al. |
| 5,231,987 A | 8/1993 | Robson |
| 5,243,980 A | 9/1993 | Mehra |
| 5,405,363 A | 4/1995 | Kroll et al. |
| 5,741,311 A | 4/1998 | McVenes et al. |
| 5,755,742 A | 5/1998 | Schuelke et al. |

(Continued)

FOREIGN PATENT DOCUMENTS

| | | |
|---|---|---|
| EP | 0288630 B1 | 11/1988 |
| EP | 2032027 B1 | 10/2011 |

OTHER PUBLICATIONS

"Agilent Impedance Measurement Handbook A Guide to Measurement Technology and Techniques 4th Edition," Agilent Technologies, Inc., Jun. 17, 2009, 140 pages.

(Continued)

*Primary Examiner* — Michael Kahelin
(74) *Attorney, Agent, or Firm* — Patterson Thuente Pedersen, P.A.

(57) ABSTRACT

Disclosed is a method for the diagnosis of conductor anomalies, such as an insulation failure resulting in a short circuit, in an implantable medical device, such as an implantable cardioverter defibrillator (ICD). Upon determining if a specific defibrillation pathway is shorted, the method excludes the one electrode from the defibrillation circuit, delivering defibrillation current only between functioning defibrillation electrodes. Protection can be provided against a short in the right-ventricular coil-CAN defibrillation pathway of a pectoral, transvenous ICD with a dual-coil defibrillation lead. If a short caused by an in-pocket abrasion is present, the CAN is excluded from the defibrillation circuit, delivering defibrillation current only between the right-ventricular and superior vena cava defibrillation coils. Determination that the defibrillation pathway is shorted may be made by conventional low current measurements or delivery of high current extremely short test pulses.

13 Claims, 6 Drawing Sheets

(56) References Cited

U.S. PATENT DOCUMENTS

| | | | |
|---|---|---|---|
| 5,897,577 | A | 4/1999 | Cinbis et al. |
| 5,944,746 | A | 8/1999 | Kroll |
| 6,104,954 | A | 8/2000 | Blunsden |
| 6,928,325 | B2 | 8/2005 | Zhu et al. |
| 7,047,083 | B2 | 5/2006 | Gunderson et al. |
| 7,081,130 | B2 | 7/2006 | Jang |
| 7,120,563 | B2 | 10/2006 | Bechhoefer et al. |
| 7,289,851 | B2 | 10/2007 | Gunderson et al. |
| 7,369,893 | B2 | 5/2008 | Gunderson |
| 7,454,249 | B1 | 11/2008 | Bornzin et al. |
| 7,747,320 | B1 | 6/2010 | Kroll et al. |
| 7,764,998 | B1 * | 7/2010 | Raddatz .............................. 607/5 |
| 8,200,330 | B2 | 6/2012 | Kroll et al. |
| 8,352,033 | B2 | 1/2013 | Kroll |
| 8,467,872 | B2 * | 6/2013 | Hareland ........................ 607/27 |
| 2004/0010303 | A1 | 1/2004 | Bolea et al. |
| 2004/0068301 | A1 | 4/2004 | Waltman et al. |
| 2004/0158290 | A1 | 8/2004 | Girouard et al. |
| 2005/0187586 | A1 | 8/2005 | David et al. |
| 2005/0256547 | A1 | 11/2005 | Stahmann et al. |
| 2006/0135886 | A1 | 6/2006 | Lippert et al. |
| 2006/0241513 | A1 | 10/2006 | Hatlestad |
| 2006/0265038 | A1 | 11/2006 | Hagen et al. |
| 2007/0208387 | A1 | 9/2007 | Mower |
| 2008/0208271 | A1 | 8/2008 | Sih et al. |
| 2008/0309351 | A1 | 12/2008 | Stewart et al. |
| 2009/0099615 | A1 | 4/2009 | Kroll |
| 2009/0292331 | A1 | 11/2009 | Gunderson et al. |
| 2010/0228307 | A1 | 9/2010 | Kroll et al. |
| 2011/0054554 | A1 | 3/2011 | Swerdlow |
| 2011/0054558 | A1 | 3/2011 | Gunderson et al. |
| 2011/0160829 | A1 | 6/2011 | Foster et al. |
| 2012/0035491 | A1 | 2/2012 | Mahajan et al. |
| 2013/0123871 | A1 | 5/2013 | Kroll |
| 2013/0325079 | A1 | 12/2013 | Kroll et al. |

OTHER PUBLICATIONS

Armour, Andrew J., et al., "Gross and Microscopic Anatomy of the Human Intrinsic Cardiac Nervous System," Anatomical Record, 1997, pp. 289-298.

Balkhy, Husam H., et al., "Autonomic Ganglionated Plexi: Characterization and Effect of Epicardial Microwave Ablation in a Canine Model of Vagally Induced Actue Atrial Fibrillation," Meeting for the International Society for Minimally Invasive Cardiothoracic Surgery (Abstract), 2006.

Brewer et al., "Low Voltage Shocks Have a Significantly Higher Tilt of the Internal Electric Field Than Do High Voltage Shocks," Angeion Corporation, Jan. 1995, Part II, PACE, vol. 18, pp. 214-220.

Chevalier, P., "Quantitative Study of Nerves of the Human Left Atrium," Heart Rhythm, 2005, pp. 518-522.

Dilling-Boer, Dagmara et al., "Ablation of Focally Induced Atrial Fibrillation: Selective or Extensive?," J. Cardio. Electryphys., 2004, pp. 200-205.

Haissaguerre, Michel et al., "Pulmonary Veins in the Substrate for Atrial Fibrillation: The "venous wave" Hypothesis," 2004, pp. 2290-2292.

Haissaguerre, Michel et al., "Spontaneous Initiation of Atrial Fibrillation by Ecoptic Beats Originating in the Pulmonary Veins," NEJM, 2006, pp. 659-666.

Kilgore, K.L., et al., "Nerve Conduction Block Utilising High-Frequency Alternating Current," Med. Biol. Eng. Comput., 2004, pp. 394-406.

Kumagai, K., et al., "Electrophysiologic Properties of Pulmonary Veins Assessed Using a Multielectrode Basket Catheter," 2004, pp. 2281-2289.

Levy, S., "Charactertization of Different Subsets of Atrial Fibrillation in General Practice in France: The ALFA Study," The College of French Cariologists, Circulation, 1999, pp. 3028-3035.

Lo et al., "Noise-Doman Reflectometry for Locating Wiring Faults," IEEE Transactions on Electromagnetic Compatibility, vol. 47, No. 1, Feb. 2005.

Nathan, H., et al., "The Junction Between the Left Atrium and the Pulmonary Veins: An Anatomic Study of Human Hearts," Circulation, 1966, pp. 412-422.

Oh., S., "Vagal Denervation and Atrial Fibrillation Inducibility: Epicardial Fat Pad Ablation Does Not Have Long-Term Effects," Heart Rhythm, 2006, pp. 701-708.

Oral, Hakan et al., "Pulmonary Vein Isolation for Paroxysmal and Persistent Atrial Fibrillation," Circulation, 2002, pp. 1077-1081.

Pappone, Carlo, "Pulmonary Vein Denervation Enhances Long-Term Benefit After Circumferential Ablation for Paroxysmal Atrial Fibrillation," Circulation, 2004, pp. 327-334.

Patterson, E. et al., "Triggered Firing in Pulmonary Veins Initiated by In Vitro autonomic nerve stimulation," Heart Rhythm, 2005, pp. 624-631.

Patterson, Eugene et al., "Sodium-Calcium Exchange Initiated by the Ca2+ Transient: An Arrhythimia Trigger Within Pulmonary Veins," J. Am. Coll. Cardiol, 2006, pp. 1196-1206.

Po Sunny S., et al., "Rapid and Stable Re-entry within the Pulmonary Vein as a Mechanism Initiating Paroxysmal Atrial Fibrillation," J.Am Coll. Cariol., 2005, pp. 1871-1877.

Po, Sunny S. et al., "Experimental Model for Paroxysmal Atrial Fibrillation Arising at the Pulmonary Vein-Atrial Junctions," Heart Rhythm, 2006, pp. 201-208.

Randall, David C., et al., "Ablation of Posterior Atrial Ganglionated Plexus Potentiates Sympathetic Tachycardia to Behavioral Stress," Comp. Physiol., 1998, pp. 779-787.

Schauerte, P., et al., "Ventricular Rate Control During Atrial Fibrillation by Cardiac Parasympathetic Nerve Stimulation: A Transvenous Approach," J. Am. Coll. Cardiol., 1999, pp. 2043-2050.

Schauerte, Patrick et al., "Catheter Ablation of Cardiac Autonomic Nerves for Prevention of Vagal Atrial Fibrillation," Circulation, 2000, pp. 2774-2780.

Schauerte, Patrick, "Focal Atrial Fibrillation: Experimental Evidence for a Pathophysiologic Role of the Autonomic Nervous System," Cardiovasc. Electrophysiol., 2001, pp. 592-599.

Scherlag, Benjamin J., et al., "Autonomically Induced Conversion of Pulmonary Vein Focal Firing Into Atrial Fibrillation," J. Am Coll. Cardiol., 2005, pp. 1878-1886.

Scherlag, Benjamin, "Electrical Stimulation to Identify Neural Elements on the Heart: Their Role in Atrial Fibrillation," J. Interv. Card, Electrophysiol, 2005, pp. 37-42.

Tai, C., "Stimulation Analysis of Conduction Block in Unmyelinated Axons Induced by High-Frequency Biphasic Electrical Currents," IEEE T-BME, 2005, p. 1323.

Tchou et al., "The AngeMed Sentinel Implantable Antitachycardia Pacer Cardioverter-Defibrillator," Implantable Cardioverter-Defibrillators: A Comprehensive Textbook, Copyright 1994, pp. 755-761.

Tomasic, "Acute and Chronic High-Frequency Properties of Cardiac Pacing and Defibrillation Leads," Med Biol Eng Comput 50:827-837, 2012.

Ellenbogen, "Performance of ICD Lead Integrity Alert to Assist in the Clinical Diagnosis of ICD Lead Failures: Analysis of Different ICD Leads," Circulation Arrhythmia and Electrophysiology, Oct. 7, 2013.

Swerdlow, "Downloadable Algorithm to Reduce Inappropriate Shocks Caused by Fractures of Implantable Cardioverter-Defibrillator Leads," Circulation Journal of the American Heart Association, Nov. 3, 2008, 9 pages.

Swerdlow, "Downloadable Software Algorithm Reduces Inappropriate Shocks Caused by Implantable Cardioverter-Defibrillator Lead Fractures—A Prospective Study," Circulation Journal of the American Heart Association, Sep. 27, 2010, 8 pages.

Application and File history for U.S. Appl. No. 12/868,056, filed Aug. 25, 2010. Inventor Swerdlow.

Application and File history for U.S. Appl. No. 13/735,599, filed Jan. 7, 2013. Inventor Kroll.

(56) References Cited

OTHER PUBLICATIONS

Application and File history for U.S. Appl. No. 13/842,838, filed Mar. 15, 2013. Inventor Kroll.

Application and File history for U.S. Appl. No. 12/252,310, filed Oct. 15, 2008. Inventor: Kroll.

Application and File history for U.S. Appl. No. 13/833,477, filed Mar. 15, 2013. Inventors: Kroll et al.

PCT Application No. PCT/US2013/043386, filed May 30, 2013, Search Report and Written Opinion dated Sep. 27, 2013, 10 pages.

PCT Application No. PCT/US2013/043389, filed May 30, 2013, Search Report and Written Opinion dated Sep. 5, 2013, 9 pages.

\* cited by examiner

METHOD FOR DETECTING AND TREATING INSULATION LEAD-TO-HOUSING FAILURES

RELATED APPLICATION

The present application claims the benefit of U.S. Provisional Application No. 61/689,191 filed Jun. 1, 2012, which is incorporated herein in its entirety by reference.

FIELD OF THE INVENTION

The present invention relates, generally, to scientific and medical methods. More particularly, the invention relates to methods for diagnosis of conductor anomalies. Most particularly, the invention relates to a method for diagnosis of conductor anomalies, such as insulation failures resulting in the shorting of a defibrillation pathway or circuit, in an implantable medical device, such as an implantable cardioverter defibrillator (ICD). Shorted defibrillation pathways are detected by measuring the impedance of the individual defibrillation pathways. If a short is identified, one electrode from the defibrillation circuit is excluded thus delivering defibrillation current only between functioning defibrillation electrodes.

BACKGROUND

The long-term reliability and safety of implantable cardiac leads is a significant issue. Anomalies of conductors in implantable medical devices constitute a major cause of morbidity. Representative examples of such medical devices include, but are not limited to, pacemakers, vagal nerve stimulators, pain stimulators, neurostimulators, and implantable cardioverter defibrillators (ICDs). For example, early diagnosis of ICD lead conductor anomalies is important to reduce morbidity and/or mortality from loss of pacing, inappropriate ICD shocks, and/or ineffective treatment of ventricular tachycardia or fibrillation (ventricular fibrillation). The early diagnosis of conductor anomalies for implantable cardiac leads is a critically important step in reducing these issues and making ICDs safer.

Multilumen ICD defibrillation electrodes or leads include one or more high-voltage conductors and one or more pace-sense conductors. The leads can be implanted as subcutaneous or intravascular leads. Insulation failures have been known to result in a functional failure of the corresponding conductor. Functional failure of a pace-sense conductor may result in symptoms caused by loss of pacing functions for bradycardia, cardiac resynchronization, or antitachycardia pacing. Functional failure of a high-voltage conductor may result in fatal failure of cardioversion or defibrillation.

Thus, one major goal is high sensitivity of diagnosis: identification of lead insulation failures at the subclinical stage, before they present as a clinical problem. A second major goal is high specificity: a false positive provisional clinical diagnosis of lead insulation failure may trigger patient anxiety and lead to potentially avoidable diagnostic testing. A false positive clinical diagnosis of insulation failure results in unnecessary lead replacement, with corresponding expense and surgical risk. Any clinical method for detecting conductor anomalies in implanted leads must make measurements while the conductor and lead are in the body.

In addition to limited sensitivity, present methods for diagnosing lead conductor anomalies have limited specificity resulting in false positive diagnostics. Evaluation of false positive diagnostics adds cost and work to medical care and may contribute to patient anxiety. If a false-positive diagnostic is not diagnosed correctly, patients may be subject to unnecessary surgical lead replacement with its corresponding risks. In the only report on this subject, 23% of leads extracted for the clinical diagnosis of lead fracture tested normally after explant.

Insulation failures occur most commonly at three regions along the course of a pacemaker or ICD lead. The first region is within the pocket, caused either by abrasion of the lead insulation by pressure from the housing ("CAN") of the pulse generator or twisting of the lead within the pocket. The second region is that between the clavicle and first rib, where the lead is subject to "clavicular crush." The third region is the intracardiac region between or under the shock coils. This third region is a particularly common site of insulation failure for the St. Jude Riata® lead which is subject to "inside-out" insulation failure due to motion of the internal cables relative to the outer insulation. In this case, inside-out abrasion of the cable to the right-ventricular shock coil may abrade against the proximal (superior vena cava) shock coil, resulting in a short circuit within the lead.

Most commonly, insulation failures of ICD defibrillation leads within the pocket can result in abrasion of the insulation around the conductor of the right-ventricular defibrillation coil (coil-CAN abrasion). This abrasion results in a short circuit between the CAN electrode and the right ventricular defibrillation coil. This short circuit prevents defibrillation current from reaching the heart in the event of life threatening ventricular tachycardia or fibrillation. In the case where the shock is delivered, extremely high current flowing through the shorted output circuit of the ICD may irrevocably damage the generator's components. Thus, many modern ICDs contain circuits to protect the ICD against shorted high voltage outputs by aborting the shock if the current in the output circuit is sufficiently high during a shock. However, even though such protective circuitry prevents damage to the generator, it also detrimentally withholds potentially lifesaving therapy from the patient.

Existing technology for diagnosis of conductor anomalies in an ICD lead is believed to have significant limitations and shortcomings. What is desired is a method that could analyze and identify implantable cardiac lead conductor anomalies at the subclinical stage, before they present as a clinical problem, and do so with a high sensitivity and specificity that minimizes false positives for implantable cardiac lead conductor anomalies. In particular, a method for timely and accurate diagnosis of insulation failures of ICD defibrillation leads within the pocket that results in a short circuit between the CAN electrode and the right-ventricular defibrillation coil is needed.

SUMMARY OF THE INVENTION

The disclosed method relates to the diagnosis of conductor anomalies, such as an insulation failure resulting in a short circuit, in an implantable medical device, such as an implantable cardioverter defibrillator (ICD). In various embodiments, a method determines if a specific defibrillation pathway is shorted, and if such a short is present, excludes the one electrode from the defibrillation circuit, delivering defibrillation current only between functioning defibrillation electrodes.

One embodiment provides protection against a short in the right ventricular coil-CAN defibrillation pathway of a pectoral, transvenous ICD with a dual-coil defibrillation lead. If a short caused by an in-pocket abrasion is present, this embodiment excludes the CAN from the defibrillation circuit, delivering defibrillation current only between the right ventricular and superior vena cava defibrillation coils. Determination that the defibrillation pathway is shorted may be made by conventional low current measurements or delivery of high current extremely short test pulses. Embodiments are described that perform testing to determine if a specific defibrillation pathway or conductor forms a short circuit with the CAN. Determination that the defibrillation pathway is shorted may be made by conventional low current measurements or delivery of high current extremely short test pulses.

An embodiment is disclosed of a basic method for detecting a short between the CAN and the RV conductor. A low voltage insulation integrity test is performed between the RV conductor and the CAN. If a short is detected then the system is set into "backup" mode meaning that the RV conductor 23 that is shorted is excluded from the defibrillation circuit and defibrillation current is only delivered between functioning defibrillation electrodes. Notification is transmitted to the physician or patient. If a short is not detected, then a high voltage insulation test is performed on a periodic basis. In one embodiment, the high voltage insulation test could be performed along with the regular capacitor/battery maintenance test.

Another embodiment is disclosed of a high voltage insulation integrity test method for detecting a short between the CAN and an RV conductor. Extremely short pulses, most generally biphasic to minimize sensation, are delivered between the RV conductor and the CAN. The test pulse in the current embodiments is a short "sliver" pulse A high voltage short is defined by a sufficient deviation from the range of normal. For example, a short can be defined by the presence of: i) an impedance of <20Ω; ii) a high voltage impedance <50% of the corresponding impedance measured with low voltage pulses, indicating voltage dependent dielectric breakdown; or iii) a ratio of high voltage to low voltage impedance significantly less than the average of the corresponding values for the last three measurements. The preferable 20Ω cutoff value could be set to any value from 0Ω to 30Ω with a better range being 5Ω to 25Ω. The percentage cutoff can be 20% to 60% or alternatively a drop of >30Ω from the low voltage value.

In one embodiment, when the capacitors are charged for regular maintenance, a plurality of sliver test pulses are delivered until the capacitor voltage attains 100 V. If a short is not detected then sliver test pulses are delivered in increasing 100V steps until the capacitor voltage attains 800 V with a determination made at each step as whether a short is detected at a particular voltage. If a short has not been detected at 800 V, the ICD is maintained in its normal mode of defibrillation.

If a short is detected at any one of the stepped test modes then the system is set to "backup" mode meaning that the shorted conductor is excluded from the defibrillation circuit and defibrillation current is only delivered between functioning defibrillation electrodes. Notification of a short circuit is transmitted to the physician or patient. In another embodiment, where a short was detected at 100 V, a "safe" voltage of 0 V is recorded as a maximum voltage for that defibrillator electrode path. If a short was detected at a higher step level, for example, 200 V, then a "safe" voltage of the previous step load, for example, 100 V is recorded as a maximum voltage for that defibrillator electrode path.

The 100 V stepped process provides a better resolution of the "safe" voltage that the insulation can withstand from a partial insulation abrasion. In other embodiments, testing may also be performed in an alternative order of pulse strength, for example, with the 800 V pulse delivered first then stepping down to 100 V, or randomly testing the various predetermined step levels.

BRIEF DESCRIPTION OF THE DRAWINGS

The invention may be more completely understood in consideration of the following detailed description of various embodiments of the invention in connection with the accompanying drawings, in which.

Figure 1:
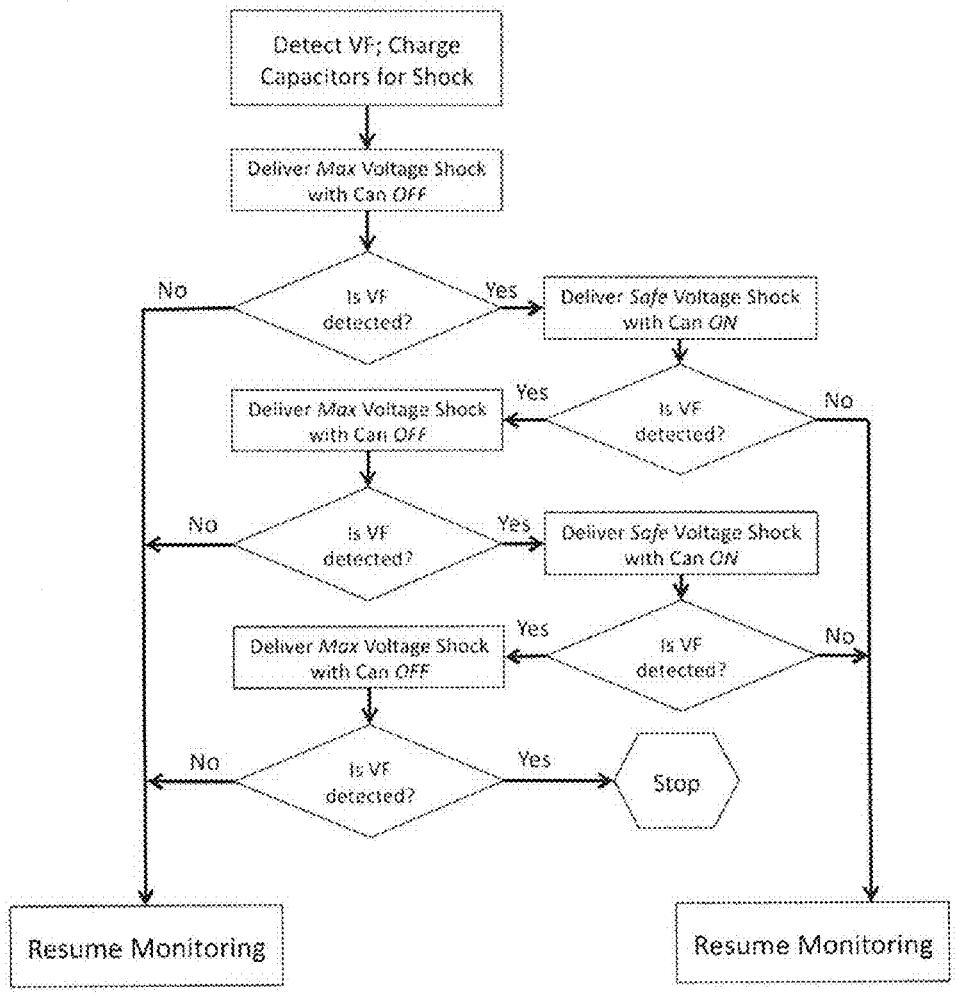
FIG. 1 depicts the backup defibrillation mode method.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

Disclosed is a method for diagnosis of conductor anomalies, such as insulation failures resulting in the shorting of a defibrillation pathway, in an implantable medical device, such as an implantable cardioverter defibrillator (ICD). Shorted defibrillation pathways are detected by measuring the impedance of the individual defibrillation pathways. If a short is identified, one electrode from the defibrillation circuit is excluded thus delivering defibrillation current only between functioning defibrillation electrodes.

Modern ICDs routinely deliver low voltage, on the order of 5 volts to 15 volts, pulses or switched AC pulse trains to assess electrical integrity of the high voltage shock pathway. However, clinical case reports indicate that life threatening insulation failures may not be detected by these low voltage measurements. Patients have died when shocks have short circuited, preventing the shock energy from reaching the heart and defibrillating ventricular fibrillation.

FIG. 1 depicts a backup defibrillation mode method which is a method of switching out the ICD housing in the event that a short is detected during the shock as disclosed in U.S. Pat. No. 7,747,320 to Kroll. However, this method typically involves a maximum voltage shock which may have enough energy to "spot weld" the exposed conductor to the housing and to ablate additional insulation which will exacerbate the insulation failure. In addition, the backup of using only the right ventricular (RV) to superior vena cava (SVC) coil-to-coil defibrillation shock is frequently unsuccessful and hence may result in a patient death. Therefore, a method of predicting such high voltage insulation failure, well in advance of a needed defibrillation, is needed.

Figure 2:
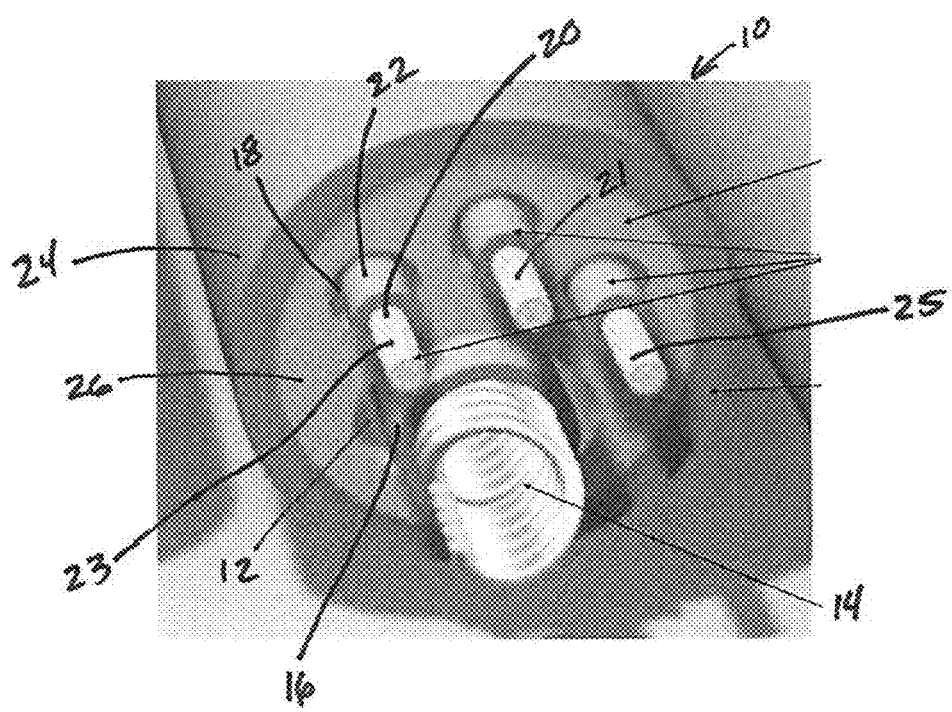
FIG. 2 depicts one example of a multilumen ICD lead.

FIG. 2 illustrates one example of an implantable cardiac lead 10. The lead 10 is comprised of a lumen 12 and center inner pacing coil 14 surrounded by PTFE insulation 16, a plurality of lumens 18 each containing at least one conductor 20 with each conductor 20 surrounded by ETFE insulation 22, an outer insulating layer 24, and a silicone insulation 26 disposed between the lumen 12 and the outer insulating layer 24. The conductors 20 include a sense conductor 21, a high voltage RV conductor 23 and a high voltage SVC conductor 25. The plurality of lumens 18 are disposed in the silicone insulation 26. The conductors 20 carry electric current to the pace-sense electrodes 66, 68, high voltage RV coil 64 and high voltage SVC coil 62 (FIG. 4).

Figure 3:
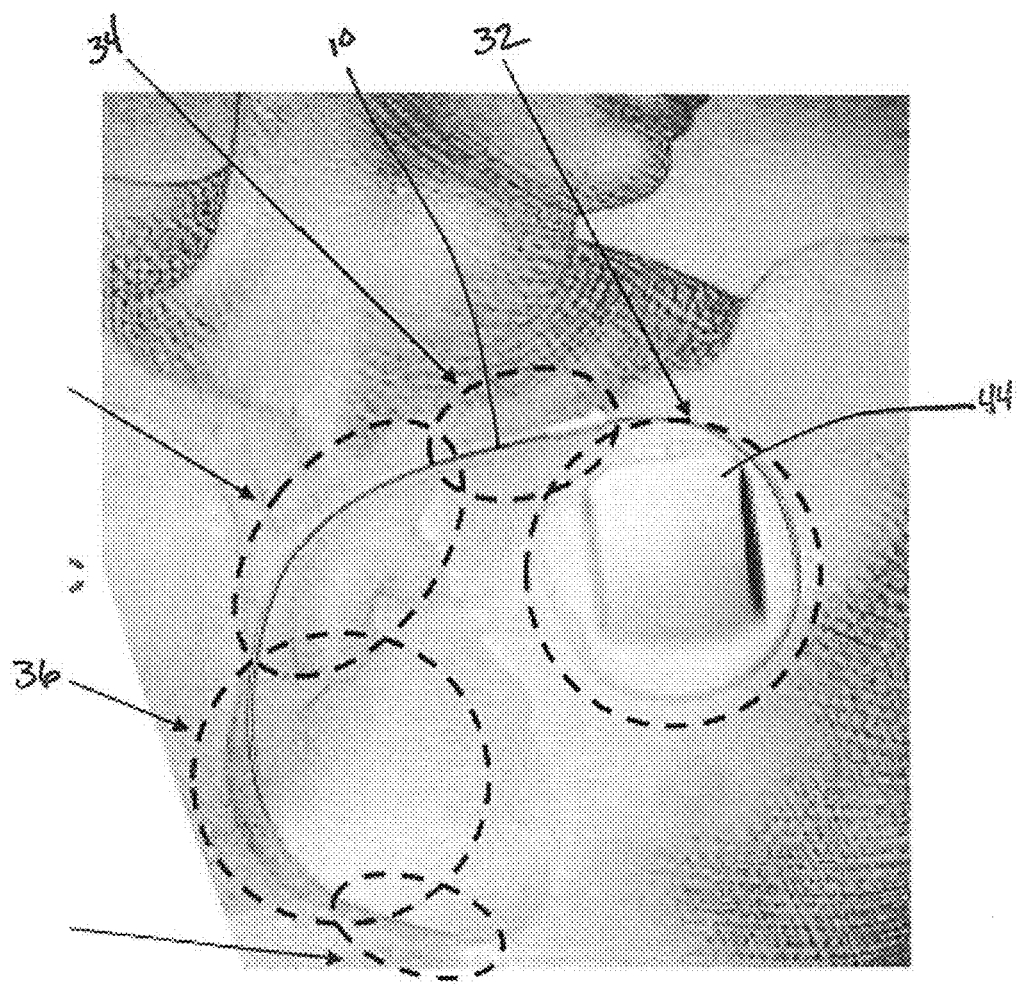
FIG. 3 illustrates regions within the human body associated with the implantation of an ICD and associated leads.

As discussed above, and shown in FIG. 3, insulation failures most commonly occur at three regions along the course of an ICD lead 10. The first region 32, and the one at issue in this disclosure, is within the pocket, caused either by abrasion of the lead 10 insulation 24 by pressure from the housing ("CAN") 44 of the pulse generator or twisting of the lead 10 within the pocket. The second region 34 is that between the clavicle and first rib, where the lead 10 is subject to "clavicular crush." The third region 36 is the intracardiac region near the tricuspid valve.

Figure 4:
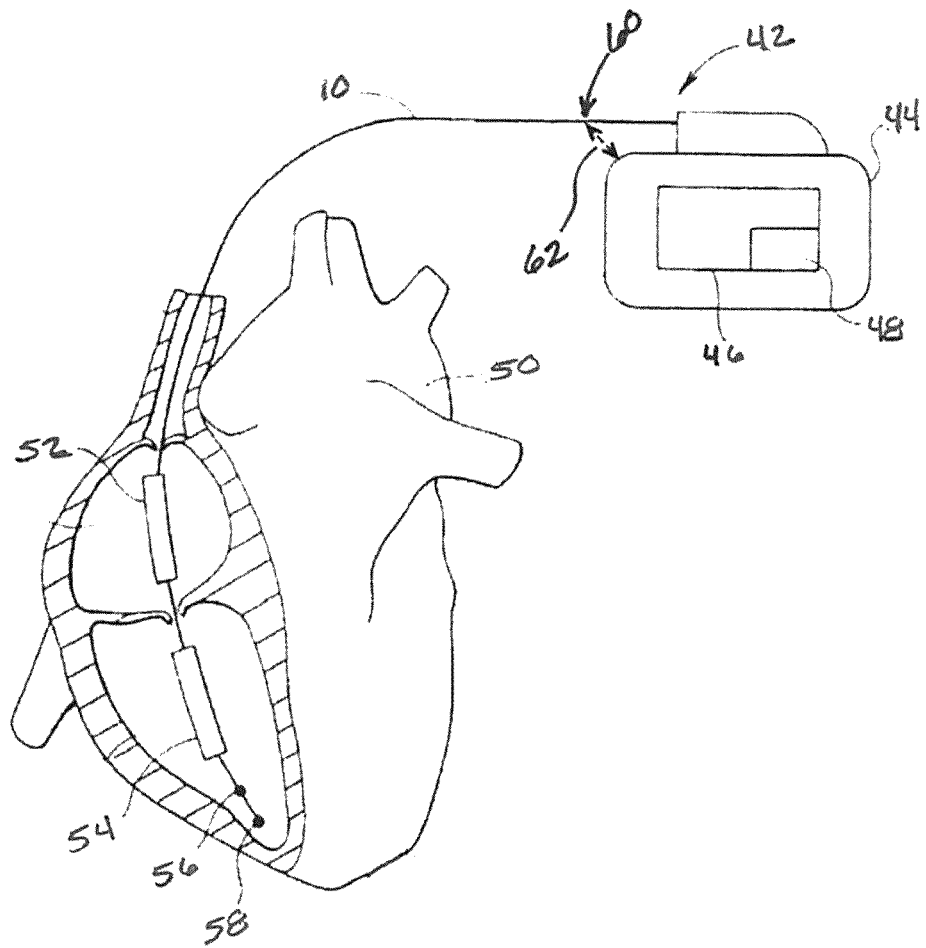
FIG. 4 shows an implantable medical device in which an embodiment of the present invention may be practiced. It shows an ICD pulse generator connected to a patient's heart via a transvenous cardiac lead used for pacing and defibrillation further illustrating a short from the RV conductor to the ICD housing.

FIG. 4 depicts on ICD 42 implanted in the chest of a patient. The ICD 42 has an outer housing 44, commonly referred to as a "CAN," inner circuitry 46 and a battery 48. Connection is made to the heart 50 via the lead 10. The lead 10 can have an optional proximal defibrillation coil 52 which is near the superior vena cava and is commonly referred to as the SVC coil 52. The lead 10 also has a distal defibrillation coil 54 which is commonly referred to as the right ventricular coil or RV coil 54. Also shown is the optional "ring" pacing-sensing electrode 56. Located at the distal end of the lead 10 is the "tip" pacing-sensing electrode 58.

The outer insulating layer 24 of the leads 10 is generally a polymer such as silicone, polyurethane, or a copolymer of silicone and polyurethane. Stress on the insulation 24 from outside-in abrasion from contact with the CAN 44, or inside-out abrasion from movement of the cables within the lead 10 may result in insulation 24 breaches or failures. In addition, the insulation 24 can fail due to chemical reactions such as metal-ion oxidation.

FIG. 4 depicts a lead 10 insulation 24 failure at location 60. In this embodiment, the insulation 24 has been abraded so that a short circuit 62 has been formed between the CAN 44 and the RV conductor 23.

Embodiments are described that perform testing to determine if a specific defibrillation pathway or conductor forms a short circuit with the CAN 44. If such a short 62 is present, the one shorted electrode is removed from the defibrillation circuit so that defibrillation current is delivered only between functioning defibrillation electrodes. One embodiment provides protection against a short in the right ventricular coil-CAN defibrillation pathway of a pectoral, transvenous ICD with a dual-coil defibrillation lead. For example, if a short caused by an in-pocket 32 abrasion is present, the invention excludes the CAN 44 from the defibrillation circuit, delivering defibrillation current only between the right ventricular 54 and superior vena cava 52 defibrillation coils. Determination that the defibrillation pathway is shorted may be made by conventional low current measurements or delivery of high current extremely short test pulses.

Figure 5:
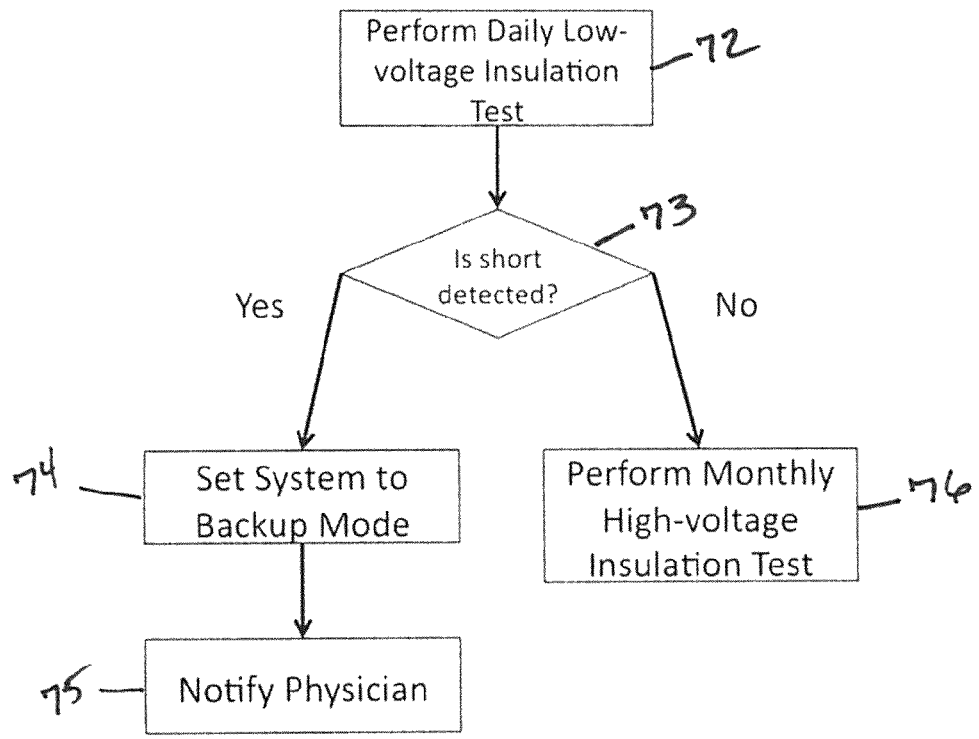
FIG. 5 is a flowchart depicting the basic method of detecting a short between the ICD housing and the RV conductor.

FIG. 5 depicts an embodiment of a basic method for detecting a short between the CAN 44 and the RV conductor 23. A low voltage insulation integrity test 72 is performed between the RV conductor 23 and the CAN 44. This test 72 can be done on a daily basis. However, the frequency of testing 72 can be modified as needed. If a short is detected 73 then the system is set into "backup" mode 74 meaning that the RV conductor 23 that is shorted is excluded from the defibrillation circuit and defibrillation current is only delivered between functioning defibrillation electrodes. Notification is transmitted to the physician 75 by, for example, remote wireless telemetry. In an embodiment, the physician or patient can be notified via a vibratory or auditory alert. If a short is not detected, then a high voltage insulation test (FIG. 6) is performed on a periodic basis 76 that is longer than the daily basis for test 72. In one embodiment, the high voltage insulation test could be performed along with the regular capacitor/battery maintenance test. The high voltage insulation test can be performed every two weeks up to once every 6 months. However, a monthly test is more likely to detect changes in the integrity of the circuit. The frequency of testing may be influenced by whether or not the lead in use is known to be particularly prone to insulation failure.

Figure 6:
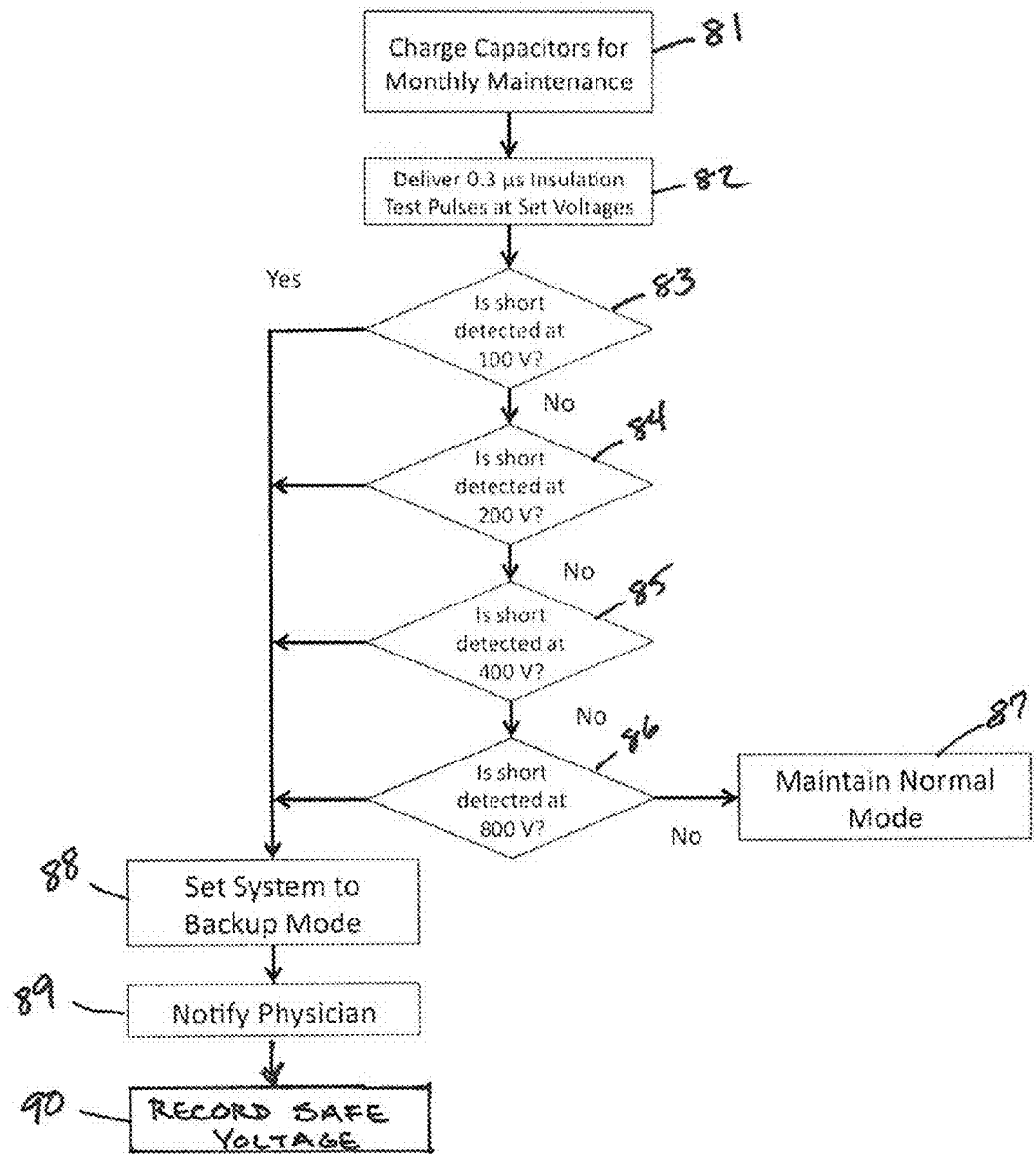
FIG. 6 is a flowchart depicting the method of detecting a short using the high voltage insulation integrity test.

FIG. 6 depicts an embodiment of a high voltage insulation integrity test method for detecting a short between the CAN 44 and an RV conductor 23. Extremely short pulses, most generally biphasic to minimize sensation, are delivered according to the teachings of U.S. Pat. No. 8,352,033, issued Jan. 8, 2013, which relevant sections are hereby incorporated by reference. However, refinement is provided herein in that the test pulse in the current embodiments is a short "sliver" pulse of 0.3 μs with an acceptable range of 0.1 μsec to 1.0 μsec in duration. Pulse durations of 1.0 μsec to 2.0 μsec are also usable but they introduce more patient sensation. Pulses may be delivered between the RV conductor 23 and the CAN 44, or between other pairs of conducting defibrillator electrodes.

A high voltage short is defined by a sufficient deviation from the range of normal. For example, a short can be defined by the presence of: i) an impedance of <20Ω; ii) a high voltage impedance <50% of the corresponding impedance measured with low voltage pulses, indicating voltage dependent dielectric breakdown; or iii) a ratio of high voltage to low voltage impedance significantly less than the average of the corresponding values for the last three measurements. The preferable 20Ω cutoff value could be set to any value from 0Ω to 30Ω with a better range being 5Ω to 25Ω. The percentage cutoff can be 20% to 60% or alternatively a drop of >30Ω from the low voltage value.

FIG. 6 involves charging the capacitors for regular maintenance 81, generally monthly. However, maintenance can be performed at any time interval as determined by the physician. Sliver test pulses 82 are delivered, as described above, until the capacitor voltage attains 100 V. Determination is made as to whether a short is detected at 100 V 83. If a short is not detected then sliver test pulses are delivered until the capacitor voltage attains 200 V and a determination is made as to whether a short is detected at this voltage 84. If a short is not detected then sliver test pulses are delivered until the capacitor voltage attains 400 V and a determination is made as to whether a short is detected at this voltage 85. If a short is not detected then sliver test pulses are delivered until the capacitor voltage attains 800 V and a determination is made as to whether a short is detected at this voltage 86. At this point, if a short has not been detected, the ICD is maintained in its normal mode 87 of defibrillation.

If a short is detected at any one of the test modes 83, 84, 85, 86 then the system is set to "backup" mode 88 meaning that the shorted conductor 23 is excluded from the defibrillation circuit and defibrillation current is only delivered between functioning defibrillation electrodes. Notification is transmitted to the physician 89 by, for example, remote wireless telemetry. In an embodiment, the physician or patient can be notified via a vibratory or auditory alert. In another embodiment, where a short was detected at 100 V, a "safe" voltage of 0 V is recorded 90 as a maximum voltage for that defibrillator electrode path. If a short was detected at a higher step level, for example, 200 V, then a "safe" voltage of the previous step load, for example, 100 V is recorded 90 as a maximum voltage for that defibrillator electrode path.

For simplicity, the voltage steps are shown as 100, 200, 400, and 800 volts in FIG. 6. It is contemplated that the high voltage insulation integrity test can be performed in 100 V steps up to the maximum output voltage. This 100 V stepped process provides a better resolution of the "safe" voltage that the insulation can withstand from a partial insulation abrasion. Alternatively, other incremental values may be utilized, e.g., 50 V and 150V. Testing may also be performed in an alternative order of pulse strength, for example, with the 800 V pulse delivered first then stepping down to 100 V.

Note that this method of FIG. 6 can be applied after ventricular fibrillation has been detected. It is anticipated that the high voltage insulation test will be performed during regular battery/capacitor maintenance, and during capacitor charging after ventricular fibrillation has been detected.

In one embodiment, the high voltage insulation test can be performed up to 400 V every month and up to 800 V every 6 months. The advantage of alternating testing voltages is the reduction in energy consumption as the 400 V shock requires <25% of the charging energy of the 800 V shock.

The values noted above are example embodiments and should not be read as limiting the scope of this invention. Those skilled in the art will recognize that the above values may be adjusted to practice the invention as necessary depending on the electrode implantable cardiac lead technology used and the physical characteristics of the patient.

While the present invention has been described with reference to certain embodiments, those skilled in the art should appreciate that they can readily use the disclosed conception and specific embodiments as a basis for designing or modifying other structures for carrying out the same purposes of the present invention without departing from the spirit and scope of the invention as defined by the appended claims.

The following patents and applications, the disclosures of which are incorporated by reference in this case (other than claims and express definitions), are prior art attempts by common inventors to solve the problem at issue: U.S. Pat. No. 8,352,033 ('033) to Kroll, issued Jan. 8, 2013; U.S. patent application Ser. No. 13/735,599 to Kroll, filed on Jan. 7, 2013 which is a continuation of '033; and U.S. patent application Ser. No. 12/868,056 to Swerdlow, filed on Aug. 25, 2010.

The following provisional applications, the disclosures of which are incorporated by reference in this case (other than claims and express definitions), are related to each other: U.S. Patent Application 61/689,191 to Kroll and Swerdlow, filed on Jun. 1, 2012; U.S. Patent Application 61/689,189 to Kroll and Swerdlow, filed on Jun. 1, 2012; and U.S. Patent Application 61/733,713 to Kroll and Swerdlow, filed on Dec. 5, 2012.

The invention claimed is:

1. A method of periodically monitoring for a potential short circuit in an implantable defibrillation system comprising:
    periodically forming a defibrillation pathway wherein the defibrillation pathway is comprised of an implantable cardioverter defibrillator generator housing (CAN) electrode and a dual-coil defibrillation lead conductor having a superior vena cava (SVC) electrode and a right ventricle (RV) electrode and a tip located in the right ventricle of a heart;measuring an impedance of the defibrillation pathway for the conductors in the defibrillation pathway using a high voltage, short duration pulse;
    determining if one of the conductors has low impedance at a level indicating a short circuit; and
    providing an indication of a potential short circuit in the implantable defibrillation system before any detection of a cardiac arrhythmia condition for which a defibrillation shock is delivered.

2. The method of claim 1, further comprising:
    measuring the impedance of the defibrillation pathway after detection of the cardiac arrhythmia condition and prior to delivering the defibrillation shock;
    determining if one of the conductors in the defibrillation pathway has low impedance at a level indicating a short circuit and, in response;
    altering delivery of the defibrillation shock into the defibrillation pathway by measuring an impedance of an RV-SVC pathway between the RV electrode and the SVC electrode; and
    if the impedance of the RV-SVC pathway does not have low impedance at a level indicating a short circuit, delivering a shock between the RV electrode and the SVC electrode; and
    if the impedance of the RV-SVC pathway does have low impedance at a level indicating a short circuit , delivering a shock between the RV electrode and the CAN electrode.

3. The method of claim 1, wherein the short is defined by an impedance of <20 Ω.

4. The method of claim 1, wherein measuring the impedance further comprises measuring the impedance using low voltages pulses, and wherein the short is defined by a high voltage impedance of <50% of a corresponding impedance measured with low voltage pulses.

5. The method of claim 1, wherein measuring the impedance further comprises measuring the impedance using low voltages pulses, and wherein the short is defined by a ratio of high voltage to low voltage impedance significantly less than the average for the corresponding values for the last measurements.

6. The method of claim 1, wherein impedance is measured for the high voltage pulse using a high current, short duration biphasic test pulse.

7. The method of claim 1, wherein the high voltage test pulse is a sliver pulse between 0.1 μsec and 2.0 μsec in duration.

8. The method of claim 1, wherein impedance is measured using a high current, short duration test pulse at successively increasing voltages.

9. The method of claim 1, wherein impedance is measured using a high current, short duration test pulse at successively decreasing voltages.

10. The method of claim 1, wherein the indication of the potential short circuit is transmitted to an external receiver.

11. The method of claim 1, wherein the indication of the potential short circuit is transmitted via an auditory or vibratory signal.

12. The method of claim 1, the defibrillation system comprising:
    the housing being an active defibrillation electrode of the generator; and
    at least two subcutaneous defibrillation electrodes, wherein the two subcutaneous defibrillation electrodes can be on the same lead.

13. The method of claim 2 wherein the defibrillation shocks alternate between housing-off shocks and safe voltage housing-on shocks.

* * * * *